US012778804B2

(12) United States Patent
O'Malley

(10) Patent No.: US 12,778,804 B2
(45) Date of Patent: Nov. 3, 2026

(54) ANTI-FOG GOGGLE WITH DETACHABLE OUTER LENS ELEMENT

(71) Applicant: Tempest Optics LLC, Portland, OR (US)

(72) Inventor: Vincent O'Malley, Portland, OR (US)

(73) Assignee: Tempest Optics, LLC, Portland, OR (US)

( * ) Notice: Subject to any disclaimer, the term of this patent is extended or adjusted under 35 U.S.C. 154(b) by 342 days.

(21) Appl. No.: 18/216,079

(22) Filed: Jun. 29, 2023

(65) Prior Publication Data

US 2025/0004307 A1 Jan. 2, 2025

(51) Int. Cl.

*A61F 9/02* (2006.01)
*G02B 7/14* (2021.01)
*H05B 3/36* (2006.01)

(52) U.S. Cl.

CPC ............. *A61F 9/026* (2013.01); *A61F 9/029* (2013.01); *A61F 2210/0033* (2013.01); *A61F 2210/009* (2013.01); *H05B 3/36* (2013.01); *H05B 2203/013* (2013.01)

(58) Field of Classification Search

CPC .. A61F 9/026; A61F 9/029; A61F 2210/0033; A61F 2210/009; H05B 3/36; H05B 2203/013; G02C 2200/02; G02C 11/08; G02B 7/14; G02B 27/0006

See application file for complete search history.

(56) References Cited

U.S. PATENT DOCUMENTS 1,963,990 A * 6/1934 Gilkeson ................ G02C 11/08 2/435
2,387,851 A * 10/1945 Lown ...................... A61F 9/028 2/441
3,024,341 A * 3/1962 Ogle, Jr. ................ A62B 18/08 128/201.15
3,484,583 A * 12/1969 Shaw, Jr. ............. H01Q 1/1278 219/203
4,209,234 A * 6/1980 McCooeye ............ G02C 11/08 219/522
4,638,728 A * 1/1987 Elenewski ............... B62J 33/00 2/435
4,682,007 A * 7/1987 Hollander .............. A42B 3/245 219/203
4,743,741 A * 5/1988 Ramus .............. B32B 17/10036 428/209

(Continued)

*Primary Examiner* — Robert H Muromoto, Jr.
(74) *Attorney, Agent, or Firm* — Schaffer IP Law, LLC

(57) ABSTRACT

A non-fogging eyewear assembly includes an outer lens assembly with an optionally heated outer transparent lens having inner and outer faces, an eyewear chassis configured to be worn by a user, and an inner lens assembly integrated within the eyewear chassis, with the inner lens assembly including an optionally heated inner transparent lens having inner and outer faces. A seal is affixed along a periphery of the outer face of the inner transparent lens assembly, and so that structure for releasably coupling the outer lens assembly to the inner lens assembly causes the outer lens to compress against and be spaced apart from the inner lens by the seal to form a gap therebetween and prevent moisture from entering the airspace that exists between the inner and outer lenses. The outer lens assembly is thus releasably decouplable from the inner lens assembly so that it can be easily replaced if damaged.

21 Claims, 6 Drawing Sheets

(56) References Cited

U.S. PATENT DOCUMENTS

| | | | | |
|---|---|---|---|---|
| 4,868,929 | A * | 9/1989 | Curcio | A61F 9/02<br>2/435 |
| 5,319,397 | A * | 6/1994 | Ryden | G02C 11/08<br>219/522 |
| 5,351,339 | A * | 10/1994 | Reuber | A42B 3/226<br>2/9 |
| 5,363,153 | A * | 11/1994 | Bailiff | G02C 11/00<br>351/158 |
| 5,459,533 | A * | 10/1995 | McCooeye | G02C 11/08<br>351/41 |
| 5,471,036 | A * | 11/1995 | Sperbeck | H05B 3/84<br>2/435 |
| 5,610,668 | A * | 3/1997 | Mage | A61F 9/028<br>2/435 |
| 5,685,722 | A * | 11/1997 | Taba | G04G 21/02<br>482/3 |
| 6,062,688 | A * | 5/2000 | Vinas | G02C 11/08<br>351/44 |
| 6,065,833 | A * | 5/2000 | Tiano | A61F 9/029<br>351/44 |
| 7,407,281 | B2 * | 8/2008 | Tagawa | G02C 11/08<br>351/158 |
| 10,582,571 | B2 * | 3/2020 | Wei | H05K 3/1258 |
| 11,472,373 | B2 * | 10/2022 | Kherani | C23C 14/0036 |
| 11,573,473 | B2 * | 2/2023 | Kubo | G02F 1/1533 |
| 11,966,141 | B2 * | 4/2024 | Rozbicki | G02F 1/153 |
| 12,148,332 | B1 * | 11/2024 | Huo | H04N 23/90 |
| 2007/0128905 | A1 * | 6/2007 | Speakman | H10F 77/244<br>257/E31.126 |
| 2018/0000648 | A1 * | 1/2018 | Mcculloch | H05B 3/06 |
| 2020/0015325 | A1 * | 1/2020 | Zhao | H05B 3/145 |
| 2020/0139935 | A1 * | 5/2020 | Kherani | G02B 5/281 |
| 2023/0112661 | A1 * | 4/2023 | Kherani | G02B 5/281<br>219/203 |

* cited by examiner

ANTI-FOG GOGGLE WITH DETACHABLE OUTER LENS ELEMENT

CROSS-REFERENCES TO RELATED APPLICATIONS

This application claims the benefit of U.S. Provisional Patent Application No. 63/356,876, filed Jun. 29, 2022, whose contents are incorporated herein for all purposes.

BACKGROUND OF THE INVENTION

Field of the Invention

The invention relates to goggles and, particularly, to anti-fog goggles having a dual lens structure where the outer lens can be detached from engagement with the inner lens for easy replacement, and where the goggles may or may not have an integrated heating element therein.

Description of the Prior Art

Goggles, as used for eye and face protection in activities ranging from industrial safety, military, and outdoor sports such as skiing and snowmobiling, often include various techniques for preventing or at least reducing the likelihood of fogging of the lens which occurs when moist warm air inside the goggle results in condensation on the inner surface of the goggle lens which has been cooled by the cold air to which the outer surface of the lens is exposed. This condensation on the inner lens creates a fog on the inner lens surface that greatly restricts visual clarity and can render the goggle unusable.

One particular and very common approach to reducing the occurrence of inner lens fogging, particularly in cold weather applications, is to utilize a double lens construction. The double lens serves to reduce the cooling effect of the outer cold air on the inner-most surface of the double lens construct, thereby lessening the likelihood of condensation on the inner lens surface. An important element of this dual lens construction is the need to prevent moisture from entering between the outer and inner lenses. Any moisture that enters this space will readily condense on the inside of the outer lens thus thwarting the purpose of the dual lens approach. In order to maintain a moisture free space between the outer and inner lenses, it is common practice to bond the outer lens to the inner lens using a waterproof adhesive gasket around the perimeter between the lenses. Given this construction, the "lens" of the goggle is actually a dual lens assembly featuring an outer lens bonded to an inner lens. This assembly is then attached to the goggle chassis using various means and the combined dual lens assembly is typically removable/replaceable by the user.

It is common for scratches to occur on the outer lens surface over time and this results in the need for the user to be able to replace the lens assembly. It is also desirable for the user to be able to configure a given goggle with different lens tints for different usage scenarios. The costs associated with this double lens assembly are relatively low and allow for low-cost lens replacements as well as the ability of the goggle vendor to offer multiple lens assemblies (featuring different lens "tints") with the purchase of a single goggle "kit" as is customarily done in the ski goggle industry. However, manipulation of this dual lens structure is still somewhat wasteful in that it requires replacement of both the inner and outer lenses together even though only the outer lens might be damaged and in need of replacement or that the aesthetics in need of replacement are only affected by the outer lens.

The conventional double lens approach as described above has limitations as to its anti-fog effectiveness and these limitations have given rise in the industry to the use of electrical assistance in the fight against fogging. This electronics-based approach relies on an electrical current that flows across the surface of the inner lens which results in the inner lens warming up to a point where condensation no longer occurs. This transmission of electrical current across the inner lens is made possible through the use of various transparent electrically conductive films that can be applied to the inner lens. Power can be provided to this lens element via a battery that is part of the goggle assembly or in some cases, externally via an electrical cable that runs from the goggle to the "power port" found on a typical snowmobile for example. In cases where the inner lens features this electrically conductive heating technique, the overall lens assembly consists of an outer lens bonded to an inner electrically conductive lens thereby forming a similar dual lens assembly to the general case dual lens assemblies.

This dual lens assembly and associated goggle chassis must make provisions for the passing of electrical current from the chassis to the heated inner lens. But there is a significant drawback to the use of this heated inner lens technique. Inclusion of a heated inner lens element carries with it a significant additional cost to the above-mentioned dual lens assembly due to the costs associated with the electrically conductive film and associated assembly labor costs. This cost addition results in potentially high lens replacement costs as well as the prohibitively higher costs associated with having multiple swappable lens tints included in a goggle kit as is typically done in the ski goggle industry.

It would thus be desirable to provide a goggle design that provides for an easily-replaceable lens in case of damage or aesthetic changes while still providing for effective anti-fog functionality.

SUMMARY OF THE INVENTION

In one aspect of the invention, a heated non-fogging eyewear assembly is described that comprises an outer lens assembly including an outer transparent lens having inner and outer faces, an eyewear chassis configured to be worn by a user, and an inner lens assembly integrated within the eyewear chassis, with said inner lens assembly including an inner transparent lens having inner and outer faces. A heating control unit is integrated into the eyewear chassis and electrically coupled to the inner lens for heating the inner lens, with a seal interposed between the outer face of the inner transparent lens and the inner face of the outer transparent lens, with said seal affixed to an outer face of the inner lens assembly and in contact with but not affixed to the inner face of the outer transparent lens.

Another aspect of the invention describes a non-fogging eyewear assembly that comprises an outer lens assembly including an outer transparent lens having inner and outer faces, an eyewear chassis configured to be worn by a user, and an optionally heated inner lens assembly integrated within the eyewear chassis, with said inner lens assembly including an inner transparent lens having inner and outer faces. A seal is affixed along a periphery of the outer face of the inner transparent lens assembly so that the means for releasably coupling the outer lens assembly to the inner lens assembly causes the outer lens to compress against and be spaced apart from the inner lens by the seal to form a gap therebetween and prevent moisture from entering the air-space that exists between the inner and outer lenses. The outer lens assembly is thus releasably decouplable from the inner lens assembly so that it can be easily replaced if damaged.

The invention described herein changes the fundamental way in which the double lens assembly is achieved. In doing so, the physical relationship between the higher cost heated inner lens, and the relatively low-cost outer lens is separated. This allows for low-cost replacements of the outer lens element as well as the inclusion of multiple lens tints in a single goggle kit without the additional cost burden of a heating element on each and every lens assembly.

To achieve this physical separation between the outer lens and inner lens, instead of permanently bonding the heated inner lens to the outer lens, the heated inner lens is included as an element of the goggle chassis. This allows the replaceable lens element to consist only of the outer lens without the burden of the costly heated inner lens. The heated inner lens always stays with the chassis, and it is the outer lens that is swapped out for a new or alternative tint lens.

The physical separation of the outer and inner lenses does not eliminate the need to achieve a moisture tight seal of the outer lens to the inner lens. Therefore, it is necessary to have a moisture tight gasket material between the outer and inner lens as well as a mechanical mechanism that holds the outer lens securely to the chassis such that no moisture can find its way inbetween the outer and inner lenses.

The foregoing and other objects, features and advantages of the invention will become more readily apparent from the following detailed description of a preferred embodiment of the invention that proceeds with reference to the accompanying drawings.

DETAILED DESCRIPTION

Figure 1:
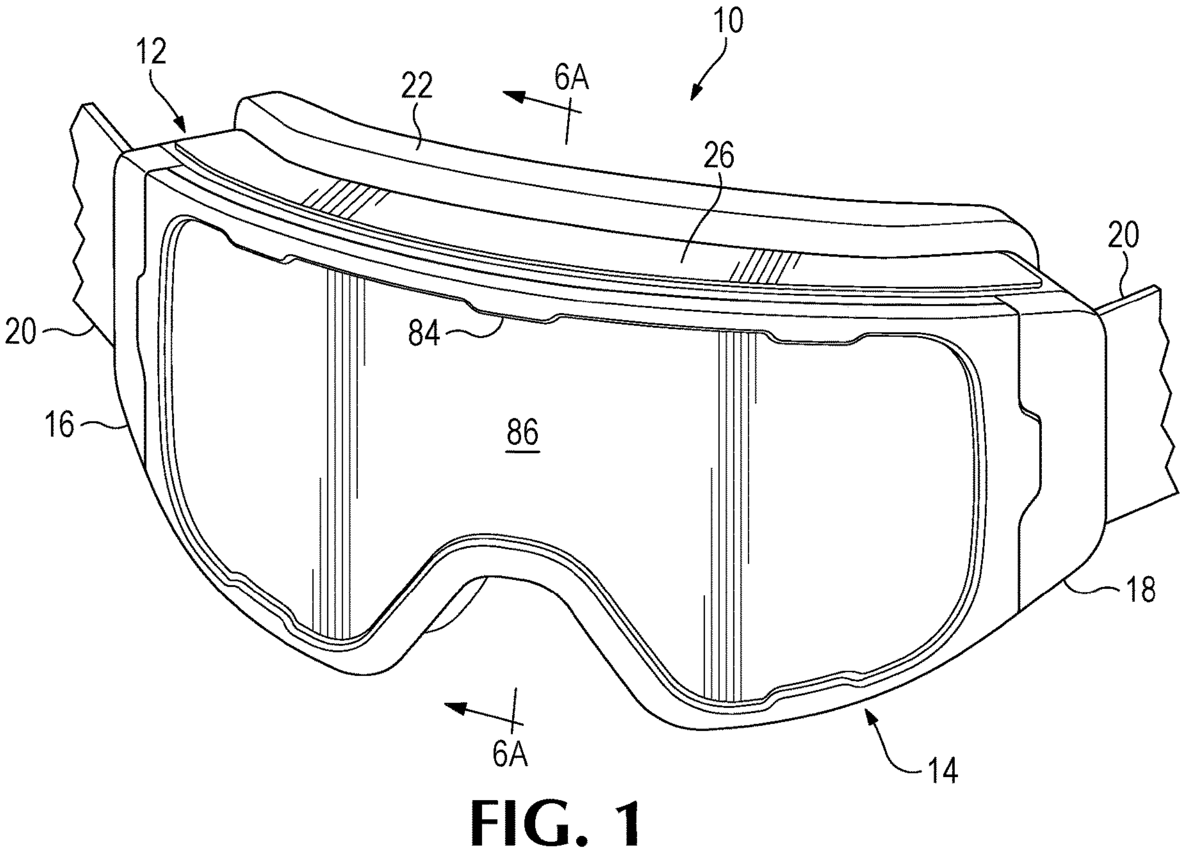
FIG. 1 is a perspective view of the anti-fog goggles configured according to teachings of the present invention.

FIG. 1 shows an anti-fog ski goggle 10 constructed according to teachings of the present invention. Goggle 10 includes a frame or chassis 12 that incorporates the lens, mount, and power control features that are described further below. As shown from the front, an outer lens assembly 14 is releasably attached to the goggle chassis 12 via means also described further below. Mount structures 16, 18 are disposed on either lateral side of the chassis 12, with a semi-elastic woven strap 20 coupled to these mount structures with the strap adapted to pass around the back of the wearer's head (or helmet) and keep the goggles firmly affixed thereto. One or more layers of foam padding 22 are adhered to a proximal peripheral portion of the goggle 10 and configured to seal against a user's face, around their eyes, and over the bridge of a user's nose. To assist with ventilation between the user's face and the inner lens assembly (described below) as well as atmospheric and humidity regulation, a series of ventilation apertures 24 (see, e.g., FIGS. 6A and 6B) are formed in a top portion of the chassis 12 and covered by ventilation foam 26.

Figure 2:
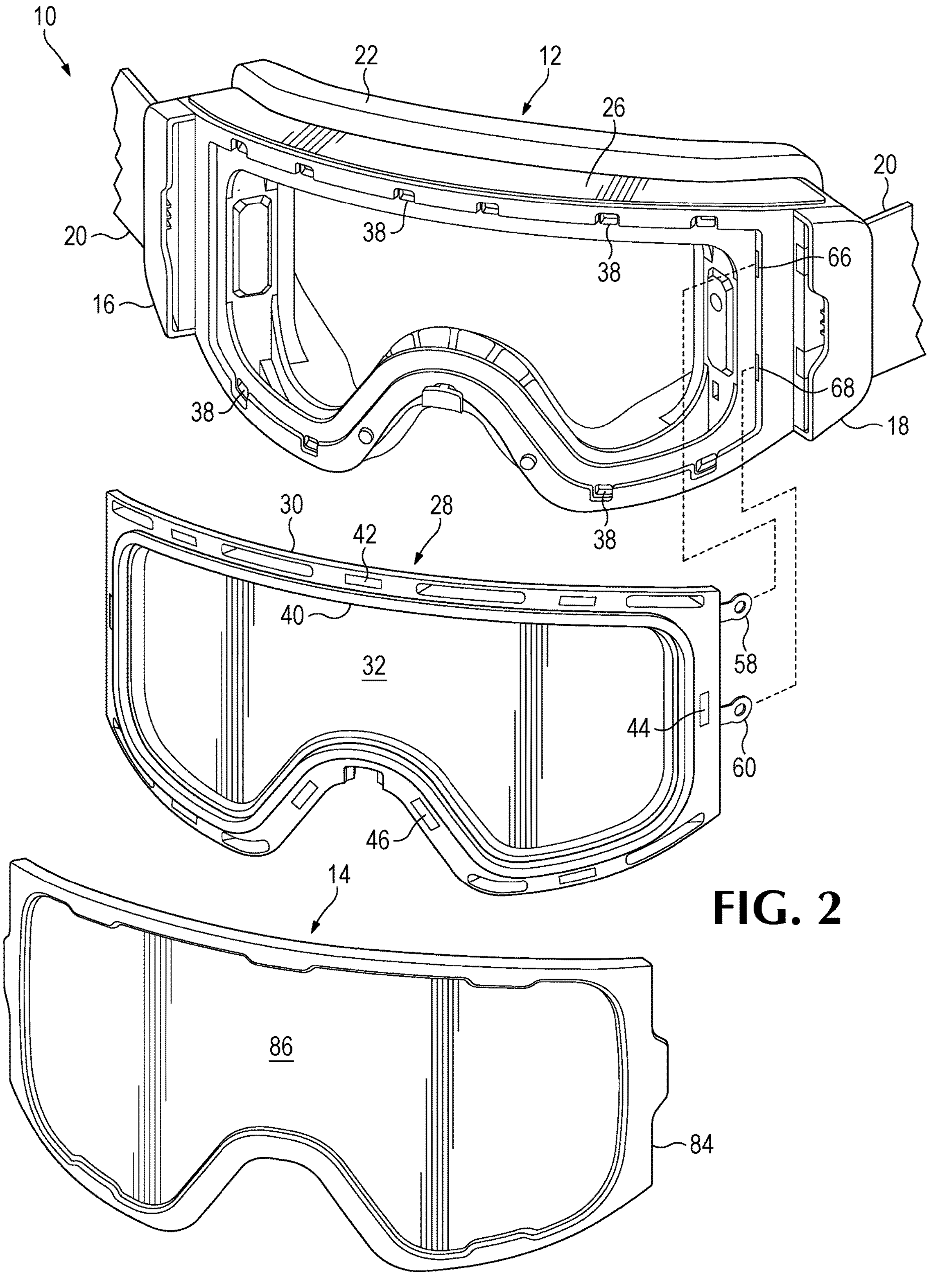
FIG. 2 is an exploded perspective view of the goggles of FIG. 1 shown from the front side.

FIG. 2 illustrates goggle 10 with the inner lens assembly 28 and outer lens assembly 14 parts exploded outward.

Figure 3:
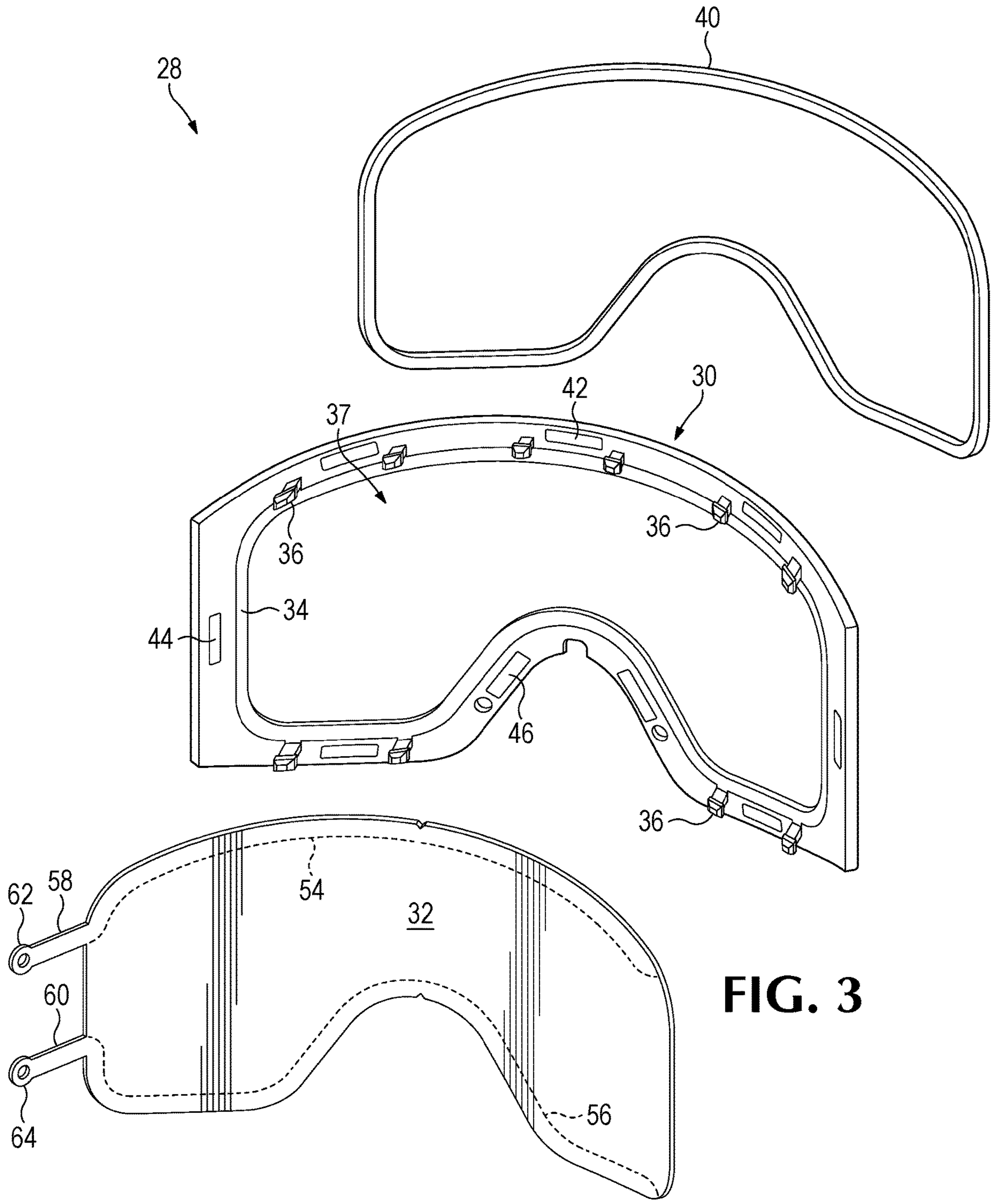
FIG. 3 is an exploded perspective view of the inner lens assembly of the goggles of FIG. 1 shown from the rear side.

As shown best in FIG. 3, inner lens assembly 28 includes an inner lens frame 30 and clear inner lens 32, with the inner lens being affixed from a proximal side (closest to a wearer's face) via an adhesive strip 34 disposed about the periphery of the lens and frame opening 37. An array of physical mating structures, here clips 36, are disposed outside of the adhesive strip 34 and are adapted to be received within a complementary array of apertures 38 disposed about the periphery of the front facing exterior of the chassis 12. The inner lens 32 is then bonded to the inner lens frame 30 via the adhesive strip 34, and the assembled inner lens assembly 28 is fixedly coupled to the goggle chassis 12 via the clips 36 and apertures 38 to form a unitary whole.

A gasket 40 is disposed about the lens frame opening on the front-facing exterior of the inner lens frame 30 and is configured to seal with the outer lens assembly 14 as described further below. Finally, an array of magnets—e.g. magnets 42, 44, and 46—are disposed outside the periphery of the gasket 40 and are configured to align and magnetically couple with the array of magnets—e.g. magnets 48, 50, 52—on the outer lens assembly 14 (see, e.g., FIG. 5) so that the completed goggle structure 10, including both the inner lens assembly 28 and outer lens assembly 14, is completed.

In one aspect of the invention, the inner lens 32 is heated by means described further below in order to further prevent fogging on the inner lens during use. Lens 32 is preferably formed of sandwiched layers of materials including an anti-fog film of cellulous acetate, an optically clear adhesive, an indium tin oxide (ITO) film adhered on either side to a polyethylene terephthalate (PET) substrate, and—on an outwardly facing surface of inner lens 32—upper and lower, electrically conductive bus bars 54, 56 disposed along a top edge and bottom edge, respectively, of the inner lens 32 outer surface. These bus bars are preferably formed of silver ink painted onto the thermally conductive ITO surface and optionally covered by a black carbon ink. Preferably, the bus bars are formed using a metallic ink layer having an asymmetric thickness across the top and bottom expanse so that the metallic ink layer is thicker closer to the heating control unit and the voltage drop along a length of the bus bar is evened out per unit length. Bus bars are individually electrically coupled to a pair of electrical connections—e.g. tabs or fingers 58, 60—that are disposed on and extend from a same lateral expanse of the inner lens 32. These fingers may be a molded extension of the lens 32 structural material with conductive material, e.g. silver ink or a copper coating, formed on the outer surfaces. Each of the fingers 58, 60 terminates in a coupling 62, 64 or terminal that includes an aperture through which a screw may be inserted in order to affix the fingers 58, 60 to a power source as discussed below. These fingers are inserted within complementary slots 66, 68 formed on an inside surface of the goggle chassis 12 and coupled directly to a heating control unit 74 when the inner lens assembly 28 is affixed to the goggle chassis 12.

Figure 4:
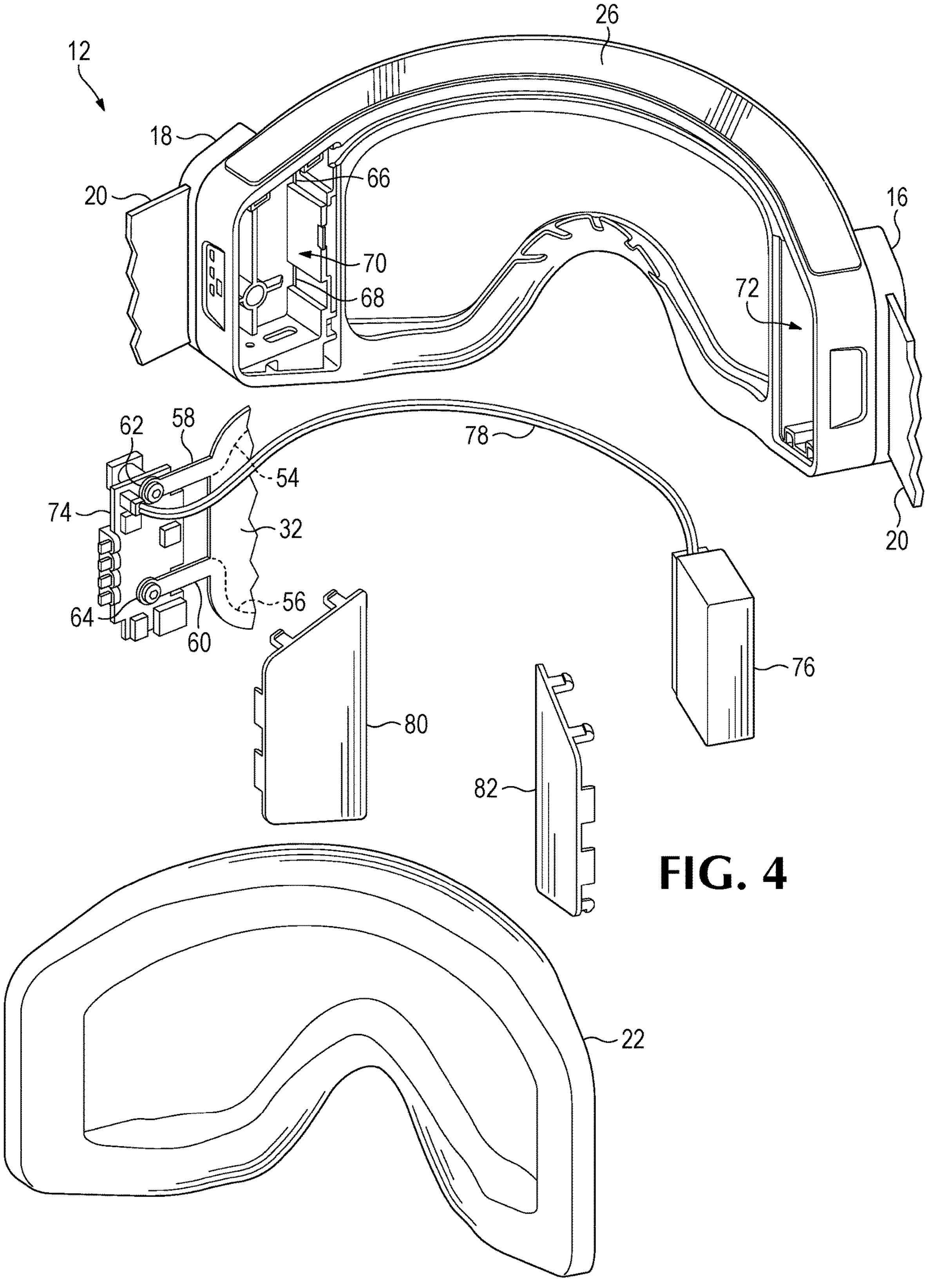
FIG. 4 is an exploded perspective view of the goggle chassis of the goggles of FIG. 1 shown from the rear side.

FIG. 4 shows the goggle chassis 12 with cavities 70, 72 formed within left and right sides, respectively, laterally outside of the frame opening 37. Cavity 70 is configured to receive a heating control unit 74 integrated into the eyewear chassis, which is electrically coupled to the inner lens 32 for heating the inner lens. Coupling preferably occurs via the electrically conductive fingers 58, 60 integrally formed within the lens 32 structure that insert through slots 66, 68 in the chassis 12 and screw onto posts on the heating control unit 74 to complete the circuit. The electrical connections then extend directly from the inner lens 32 through aligned apertures 66, 68 into the eyewear chassis 12 where a connection can be made directly to circuitry 74 within the eyewear chassis. This is made possible because the fingers 58, 60 are formed on and extend from the same lateral expanse of the inner lens 32 and can then be coupled within the same side of the goggle frame 12 to the heating control unit 74.

The heated embodiment of the goggle preferably includes a power source mounted within the eyewear chassis and electrically coupled on the heating control unit on an opposite side thereof. The heating control unit 74 is powered via a battery 76 mounted within cavity 72 on the right side of the goggle chassis 12, with power transmitted via wires 78 passing from the right to left side and plugged into the circuit board of the heating control unit 74. In a preferred embodiment, the heating control unit includes a resistance detection circuit for detecting resistance of the inner lens and a voltage adjust circuit configured to adjusting voltage applied to the inner lens responsive to the resistance detection circuit. That is, power is driven across bus bars and the applied voltage is adjusted responsive to the detected resistance across the lens. Covers 80, 82 then clip into complementary structures on the goggle frame 12 and seal the cavities, with the foam padding 22 adhered along the inside surface of the goggle frame and overtop these covers.

Figure 5:
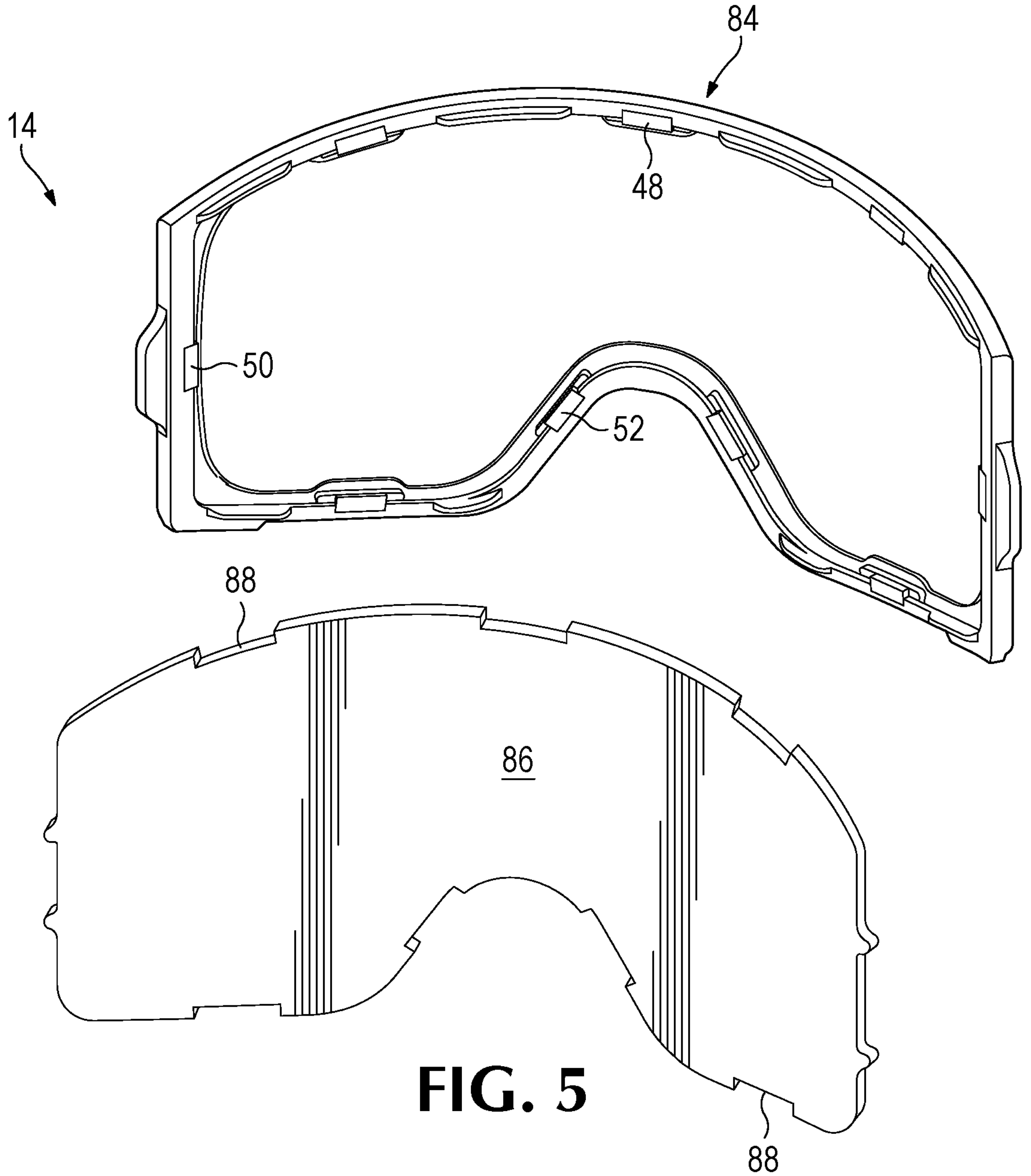
FIG. 5 is an exploded perspective view of the outer lens assembly of the goggles of FIG. 1 shown from the rear side.

FIG. 5 is an exploded view of the outer lens assembly 14 and includes the outer lens frame 84 and outer lens 86. The outer lens 86 includes an array of cutouts—such as cutout 88—that are formed to accept the array magnets 48, 50, 52 rearwardly facing on the frame 84 and retained therebetween. Outer lens 86 can then be easily detached from the goggle frame 12, as by pulling the outer lens assembly magnets 48, 50, 52 from engagement with the inner lens assembly magnets 42, 44, 46. The outer lens 86 can then be easily replaced if it is damaged, or if an aesthetic change is desired by the user such as changing the tint of the outer lens, the reflectivity, or replacing it with an outer lens having some sort of graphic.

Figure 6B:
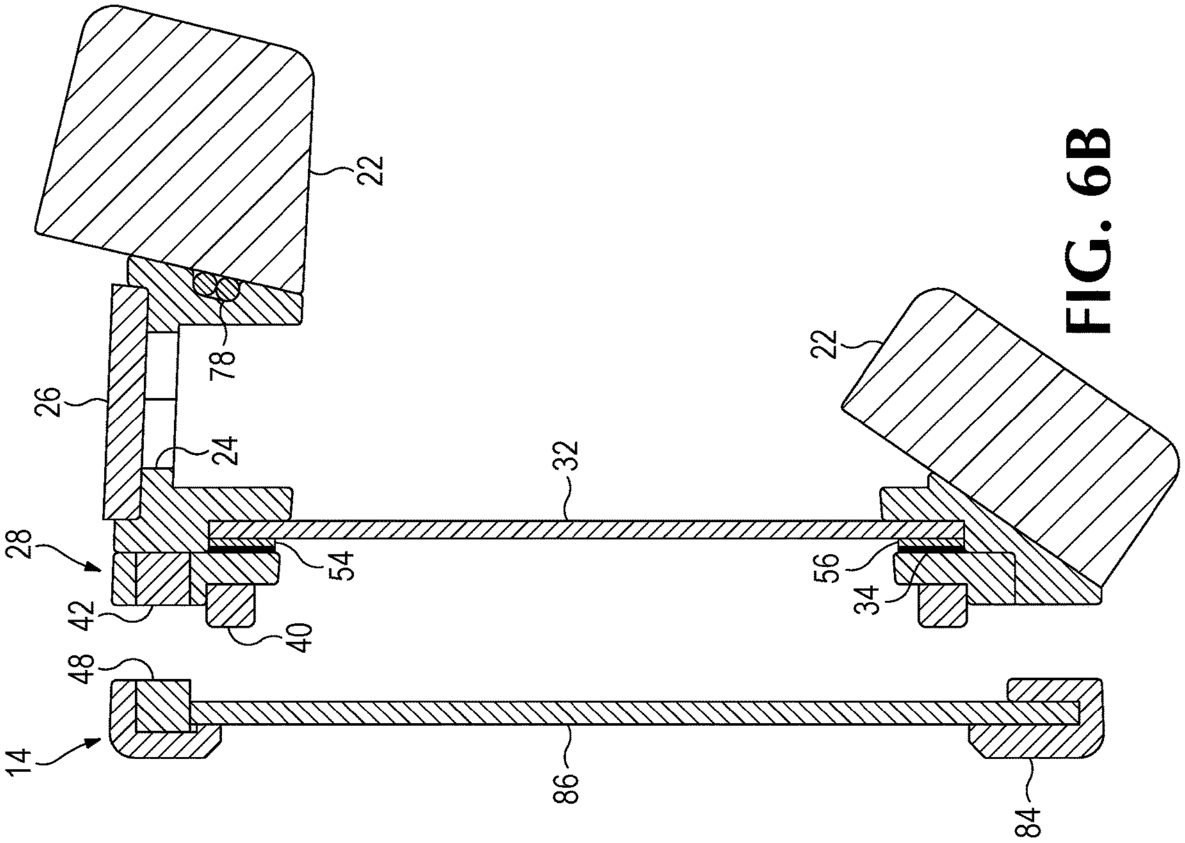
FIGS. 6A and 6B are side sectional views taken along line 6A-6A of FIG. 1 showing the outer lens assembly of the present invention in assembled and detached positions, respectively.
Figure 6A:
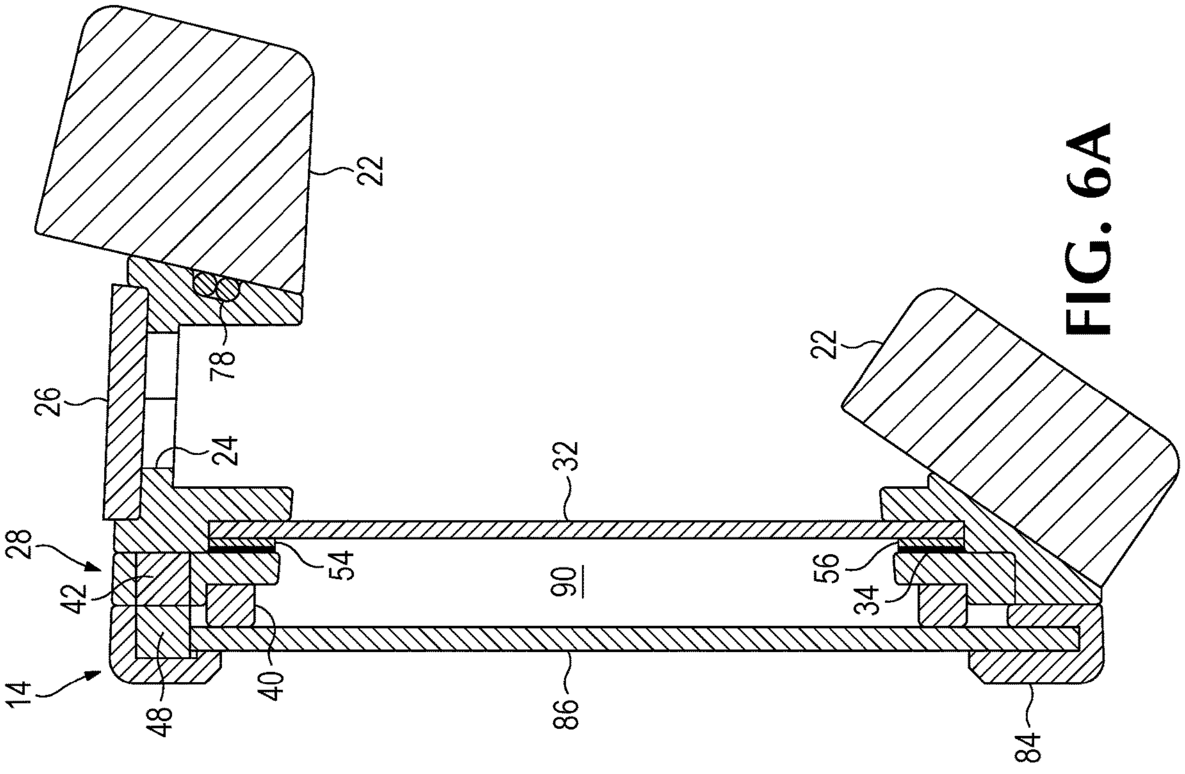

FIGS. 6A and 6B illustrate how the outer lens assembly 14 is assembled (and detached) from the inner lens assembly 28. Different means for releasably coupling the outer lens assembly to the inner lens assembly are contemplated so that the outer lens 86 can be more easily removed and replaced as needed. In a preferred aspect, the means for releasably coupling the outer lens assembly to the inner lens assembly includes an array of magnets (e.g., magnets 42, 44, 46) spaced along the periphery of the inner lens assembly, and an array of complementary magnets (e.g., magnets 48, 50, 52) spaced along the periphery of the outer lens assembly in alignment with the array of magnets of the inner lens assembly and configured to attract the outer lens assembly into engagement with the inner lens assembly, where the magnets are configured to allow a user to remove and pull away the outer lens assembly from contact with the inner lens assembly. In another aspect, the means for releasably coupling the outer lens assembly to the inner lens assembly includes an array of complementary physical structures spaced along the periphery of the inner lens assembly and outer lens assemblies that are configured to allow a user to remove the outer lens assembly from contact with the inner lens assembly. The complementary structures can include an array of tabs extending orthogonally from the periphery of the outer lens assembly and engaging with an aligned array of slots formed along the periphery of the inner lens assembly.

FIG. 6A illustrates the assembled form, where the inner surface of the outer lens 86 compresses against and is spaced apart from the inner lens 32 by the elastomeric gasket 40 to form a gap 90 therebetween. A spacing 90 between the inner face of the outer lens with the inner lens assembly when the array of magnets of the inner lens assembly is engaged with the array of magnets of the outer lens assembly is less than a thickness of the seal in an uncompressed state, so that the seal is compressed by engagement of the outer lens assembly with the remainder of the eyewear assembly and thereby contributes to formation of a sealed gap between inner and outer lenses. According to teachings of this invention, the outer lens only rests upon the seal when mated to the chassis and is not bonded to it as with other dual lens goggles so that the gasket is compressed and forms an airtight seal which prevents moisture from entering the air space between the inner and outer lenses. Replacement thus does not require that the combined two-lens structure be removed and replaced, instead only requiring that the outer lens assembly 14 be removed from engagement with the inner lens assembly 28 as shown in FIG. 6B, thus making repair or replacement easier and less expensive where the outer lens 86 and assembly can be releasably decouplable from the inner lens assembly so that it can be easily replaced if damaged.

Whereas the heating circuit has in the past been generally part of the replaceable lens assembly, the present invention integrates the heated inner lens in the goggle chassis itself. One approach to achieve this integration of heated lens and chassis is to bond the heated lens to a lens frame and then attach the heated lens frame to the chassis using snap features that are built into the lens frame and chassis. Another approach would be to bond the heated lens directly to the chassis without the use of the additional lens frame.

Because the heated lens draws power from a power source, structure is required to connect the heated lens to this power source. A preferred approach as noted herein is to design the heated lens such that electrically conductive "tales" extend directly from the lens into the chassis where a connection can be made directly to a circuitry within the goggle chassis. Alternatively, the heated lens could contain metallic electrical contacts that mount to the lens frame which come in contact with metallic electrical contacts located on the chassis which deliver power from the power source to the heated lens. A further alternative is to connect the lens tales directly to an electrical connector in the chassis which in turn could be connected to a power source located external to the goggle chassis such as a battery pack located on the goggle strap.

A primary feature to one aspect of the invention is the fact that the outer lens exists as a separate and replaceable element apart from the heated inner lens which, in this invention, is part of the goggle chassis. Thus, a mechanical mechanism is required that allows this outer lens to be attached to the chassis in such a way as to create the double lens sandwich in which there is a moisture proof gasket between the outer and inner lenses which prevents moisture from entering into the airspace between these two lenses.

One approach is to use an outer lens frame into which the outer lens is mounted, and then to equip this outer lens frame with a number of magnets around its perimeter which, through magnetic attraction, mate with a number of magnets located within the chassis. Another approach would be to rely on mechanical clips located along either the chassis perimeter or the outer lens perimeter that can latch the outer lens to the goggle chassis.

Finally, an essential aspect of this invention is that when the outer lens is mated to the chassis in which the inner lens is contained, a seal that extends around the entire perimeter of the mated lenses must be achieved which will prevent moisture from entering the airspace that exists between the two lenses. One approach to implementing such a moisture barrier is to include in the heated lens frame or chassis, an elastomeric gasket onto which the outer lens will rest when mated to the chassis. When the outer lens is attached to the chassis via magnets or a physical latching mechanism, the soft gasket material is compressed and forms an airtight seal which prevents moisture from entering the air space between the two lenses.

As described above, dual lens assemblies featuring an electrically conductive heated inner lenses carry significantly higher costs than do dual lens assemblies with passive inner lenses. This is because of the higher costs associated with the heated inner lens technology and construction. And since these dual lens assemblies have typically consisted of an outer lens bonded to the relatively expensive inner lens, the overall lens assembly costs are significantly higher than the passive double lens offerings. This cost premium results in expensive lens replacements and makes it commercially unfeasible to include multiple lens tints with the purchase of a single goggle. This is a competitive disadvantage to goggle offerings that feature dual passive lens assemblies and is an aspect of design that the present invention solves.

In summary, therefore, anti-fog goggles are described with a two-layer lens system that is configured for easier replacement of a damaged outer lens. To achieve a physical separation between the outer lens and inner lens, and instead of permanently bonding the heated inner lens to the outer lens, a heated inner lens is included as an element of the goggle chassis. This allows the replaceable lens element to consist only of the outer lens without the burden of the costly heated inner lens. The heated inner lens always stays with the chassis, and it is the outer lens that is swapped out for a new or alternative tint lens. That is, the heated inner lens is part of the goggle chassis itself as opposed to being a part of the replaceable lens assembly. The outer lens exists as a separate and replaceable element apart from the heated inner lens part of the goggle chassis, and a seal extends around the entire perimeter of the mated lenses to prevent moisture from entering the airspace that exists between the two lenses.

In other aspects, a mechanical mechanism is required that allows this outer lens to be attached to the chassis in such a way as to create the double lens sandwich in which there is a moisture proof gasket between the outer and inner lenses which prevents moisture from entering into the airspace between these two lenses. Regarding the elastomeric gasket, the outer lens is adapted to rest on this so that when the outer lens is attached to the chassis via magnets or a physical latching mechanism, the soft gasket material is compressed and forms an air tight seal which prevents moisture from entering the air space between the two lenses. The heated lens is bonded to the lens frame, and the heated lens is connected directly to a power source. The heated lens frame can be attached to the chassis using snap features that are built into the lens frame and chassis, and the outer lens captured within an outer lens frame into which the outer lens is mounted whereby the outer lens frame includes a number of magnets around its perimeter that mate with a number of magnets located within the chassis. Alternatively, mechanical clips located along either the chassis perimeter or the outer lens perimeter can latch the outer lens to the goggle chassis.

Although the embodiment shown in the figures includes an inner frame, the heated lens may be bonded directly to the chassis without the use of the additional lens frame and the electrically conductive "tales" extended directly from the lens into the chassis where a connection can be made directly to a circuitry within the goggle chassis. That is, the heated lens could contain metallic electrical contacts that mount to the lens frame which come in contact with metallic electrical contacts located on the chassis which deliver power from the power source to the heated lens. The lens tales could connect directly to an electrical connector in the chassis which in turn could be connected to a power source located external to the goggle chassis such as a battery pack located on the goggle strap. Bus bar connections are preferably located on same side of the lens, which distinguishes from conventional systems where such connections are on opposed sides, with differentiating bus bar thicknesses in order to regulate potential across the lens. In one aspect, resistance is reduced by using extra silver ink or, alternatively, using thicker ink layer across half of bus bars.

Having described and illustrated the principles of the invention in a preferred embodiment thereof, it should be apparent that the invention can be modified in arrangement and detail without departing from such principles where, for instance, inventive goggle is not just limited to particular means for releasably coupling the outer lens assembly from the inner lens assembly. Or that the mechanism for attaching the strap to the goggle frame can include extensions so that the strap extends around and fits over a helmet for use with snowmobiling and the like.

What is claimed is:

1. A heated non-fogging eyewear assembly, comprising:

an outer lens assembly including an outer transparent lens having inner and outer faces;

an eyewear chassis configured to be worn by a user;

an inner lens assembly fixedly coupled to the eyewear chassis and in engagement with said outer lens, with said inner lens assembly including an inner transparent lens having inner and outer faces;

a heating control unit integrated into the eyewear chassis and electrically coupled to the inner lens for heating the inner lens;

a seal interposed between the outer face of the inner transparent lens and the inner face of the outer transparent lens, with said seal affixed to an outer face of the inner lens assembly and in contact with but not affixed to the inner face of the outer transparent lens so that the outer lens assembly is capable of being selectively detached from engagement with the inner lens assembly as the inner lens assembly remains fixedly coupled to the eyewear chassis and the eyewear chassis remains worn by the user; and an array of magnets spaced along the periphery of the inner lens assembly outside a periphery of the seal, and an array of complementary magnets spaced along the periphery of the outer lens assembly in alignment with the array of magnets of the inner lens assembly and configured to attract the outer lens assembly into engagement with the inner lens assembly and compress the seal therebetween, said magnets configured to allow a user to remove and pull away the outer lens assembly from engagement with the inner lens assembly.

2. The heated non-fogging eyewear assembly of claim 1, further including an array of complementary structures spaced along the periphery of the inner lens assembly and outer lens assemblies that are configured to allow a user to remove the outer lens assembly from contact with the inner lens assembly.

3. The heated non-fogging eyewear assembly of claim 2, wherein the complementary structures include an array of tabs extending orthogonally from the periphery of the outer lens assembly and engaging with an aligned array of slots formed along the periphery of the inner lens assembly.

4. The heated non-fogging eyewear assembly of claim 1, where the inner lens assembly includes an inner lens frame into which the inner transparent lens is bonded.

5. The heated non-fogging eyewear assembly of claim 1, further including a pair of electrical connections disposed on a same lateral expanse of the inner lens and coupled directly to the heating control unit.

6. The heated non-fogging eyewear assembly of claim 5, wherein the electrical connections extend directly from the inner lens through aligned apertures into the eyewear chassis where a connection can be made directly to circuitry within the eyewear chassis.

7. The heated non-fogging eyewear assembly of claim 5, further including a power source mounted within the eyewear chassis and electrically coupled on the heating control unit on an opposite side thereof.

8. The heated non-fogging eyewear assembly of claim 1, wherein the seal includes an elastomeric gasket onto which the outer lens will rest when mated to the chassis so that the gasket is compressed and forms an airtight seal which prevents moisture from entering the air space between the inner and outer lenses.

9. The heated non-fogging eyewear assembly 1, further including bus bars in spaced apart orientation along top and bottom expanses of the inner lens, with said bus bars being in electrical contact with the heating control unit.

10. The heated non-fogging eyewear assembly of claim 9, wherein the bus bars are formed using a metallic ink layer having an asymmetric thickness across the top and bottom expanse so that the metallic ink layer is thicker closer to the heating control unit and the voltage drop along a length of the bus bar is evened out per unit length.

11. The heated non-fogging eyewear assembly of claim 9, wherein the inner lens includes a thermally conductive transparent indium tin oxide (ITO) layer formed on the outside face of the inner lens and conductively coupled to the bus bars.

12. The heated non-fogging eyewear assembly of claim 1, wherein the heating control unit includes a resistance detection circuit for detecting resistance of the inner lens and a voltage adjust circuit configured to adjust voltage applied to the inner lens responsive to the resistance detection circuit.

13. A non-fogging eyewear assembly, comprising:
- an outer lens assembly including an outer transparent lens having inner and outer faces;
- an eyewear chassis configured to be worn by a user;
- a strap coupled to the eyewear chassis and configured to keep the chassis firmly affixed to a wearer's head;
- an inner lens assembly fixedly coupled to the eyewear chassis, with said inner lens assembly including an inner transparent lens having inner and outer faces;
- a seal affixed along a periphery of the outer face of the inner transparent lens assembly; and
- means for releasably coupling the outer lens assembly to the inner lens assembly including an array of magnets spaced along the periphery of the inner lens assembly, and an array of complementary magnets spaced along the periphery of the outer lens assembly in alignment with the array of magnets of the inner lens assembly so that the inner surface of the outer lens is biased toward and compresses against and is spaced apart from the inner lens by the seal to form a gap therebetween and prevent moisture from entering the airspace that exists between the inner and outer lenses, the outer lens assembly being releasably decouplable from the inner lens assembly as the inner lens assembly remains fixedly coupled to the eyewear chassis and the chassis remains firmly affixed to the wearer's head so that the outer lens assembly can be easily replaced without removing the chassis from the wearer's head.

14. The non-fogging eyewear assembly of claim 13, wherein a spacing between the inner face of the outer lens with the inner lens assembly when the array of magnets of the inner lens assembly is engaged with the array of magnets of the outer lens assembly is less than a thickness of the seal in an uncompressed state, so that the seal is compressed by engagement of the outer lens assembly with the remainder of the eyewear assembly and thereby contributes to formation of a sealed gap between inner and outer lenses.

15. The non-fogging eyewear assembly of claim 13, further including a heating control element integrated into the eyewear chassis and electrically coupled with the inner lens assembly for imparting an electrical charge across the inner lens to thereby heat the inner lens.

16. A heated non-fogging eyewear assembly, comprising:
- an outer lens assembly including an outer transparent lens having inner and outer faces;
- an eyewear chassis configured to be worn by a user;
- an inner lens assembly fixedly coupled to the eyewear chassis and in engagement with said outer lens, with said inner lens assembly including an inner transparent lens having inner and outer faces;
- a heating control unit integrated into the eyewear chassis and electrically coupled to the inner lens for heating the inner lens;
- a seal interposed between the outer face of the inner transparent lens and the inner face of the outer transparent lens, with said seal affixed to an outer face of the inner lens assembly and in contact with but not affixed to the inner face of the outer transparent lens so that the outer lens assembly is capable of being selectively detached from engagement with the inner lens assembly as the inner lens assembly remains fixedly coupled to the eyewear chassis and the eyewear chassis remains worn by the user; and
- bus bars in spaced apart orientation along top and bottom expanses of the inner lens, with said bus bars being in electrical contact with the heating control unit, wherein the bus bars are formed using a metallic ink layer having an asymmetric thickness across the top and bottom expanse so that the metallic ink layer is thicker closer to the heating control unit and the voltage drop along a length of the bus bar is evened out per unit length.

17. The heated non-fogging eyewear assembly of claim 16, further including an array of complementary structures spaced along a periphery of the inner lens assembly and outer lens assemblies that are configured to allow a user to remove the outer lens assembly from contact with the inner lens assembly.

18. The heated non-fogging eyewear assembly of claim 17, wherein the complementary structures include an array of tabs extending orthogonally from the periphery of the outer lens assembly and engaging with an aligned array of slots formed along the periphery of the inner lens assembly.

19. The heated non-fogging eyewear assembly of claim 16, further including a pair of electrical connections disposed on a same lateral expanse of the inner lens and coupled directly to the heating control unit.

20. The heated non-fogging eyewear assembly of claim 19, wherein the electrical connections extend directly from the inner lens through aligned apertures into the eyewear chassis where a connection can be made directly to circuitry within the eyewear chassis.

21. The heated non-fogging eyewear assembly of claim 19, further including a power source mounted within the eyewear chassis and electrically coupled on the heating control unit on an opposite side thereof.

* * * * *